United States Patent [19]
Hoyle et al.

[11] Patent Number: 6,034,150
[45] Date of Patent: Mar. 7, 2000

[54] POLYMERIZATION PROCESSES USING ALIPHATIC MALEIMIDES

[75] Inventors: Charles E. Hoyle; Shan Christopher Clark, both of Hattiesburg, Miss.; E. Sonny Jönsson, Stockholm, Sweden

[73] Assignees: University of Southern Mississippi, Hattiesburg, Miss.; First Chemical Corp., Pascagoula, Miss.

[21] Appl. No.: 08/917,024

[22] Filed: Aug. 22, 1997

Related U.S. Application Data

[60] Provisional application No. 60/024,546, Aug. 23, 1996.

[51] Int. Cl.[7] ............................... C08F 2/46; C08F 2/48; C08F 20/18; C08F 22/40
[52] U.S. Cl. ........................... 522/63; 522/167; 522/178; 522/181; 522/182
[58] Field of Search ............................. 522/168, 63, 167, 522/107, 141, 142, 181, 182, 178

[56] References Cited

U.S. PATENT DOCUMENTS

| | | |
|---|---|---|
| 3,729,814 | 5/1973 | Wright et al. |
| 4,287,294 | 9/1981 | Rubner et al. |
| 4,329,556 | 5/1982 | Rubner et al. |
| 4,416,975 | 11/1983 | Green et al. |
| 4,544,621 | 10/1985 | Roth . |
| 4,626,497 | 12/1986 | Roth et al. |
| 4,656,292 | 4/1987 | Roth . |
| 4,886,842 | 12/1989 | Drain et al. ........................ 522/103 |
| 5,171,655 | 12/1992 | Aoshima . |
| 5,196,550 | 3/1993 | Long, II et al. |
| 5,319,101 | 6/1994 | Long, II et al. |
| 5,446,073 | 8/1995 | Jonsson et al. |

FOREIGN PATENT DOCUMENTS

| | | |
|---|---|---|
| 0 094 913 | 11/1983 | European Pat. Off. |
| 0 410 794 | 1/1991 | European Pat. Off. |
| 4 024 710 | 2/1991 | Germany . |
| 3 084 016 | 4/1991 | Japan . |
| 04 161 413 | 6/1992 | Japan . |

OTHER PUBLICATIONS

Woo–Sik Kim et al., "Synthesis and Photocrosslinking of Maleimide–Type Polymers," *Macromol. Rapid Commun.*, vol. 17, No. 11, pp. 835–841, Nov., 1996.

Chemical Abstracts, vol. 91, No. 6, Aug. 6, 1979, Columbus, Ohio, US; abstract No. 39958x, Shulyndin S.V. et al., "Synthesis and Properties of Polymers Containing Phosphorus and Nitrogen," p. 39962.

J. Put and F.C. DeSchryver, "Photochemistry of Nonconjugated Bichromophoric Systems. Intramolecular Photocycloaddition of N,N'–Alkylenedimaleimides in Solution," *J. Amer. Chem. Soc.*, 95, 140, Jan. 10, 1973.

F.C. DeSchryver, N. Boens and G. Smets, "Photopolymerization V. Unsensitized Solution Photocyclopolymerization of N,N'–Alkylenebismaleimides," *Journal of Polymer Science*, vol. 10, 1687–1699 (1972).

F.C. DeSchryver, W.J. Feast and G. Smets, Photocycloaddition Polymerization. I. Preparation and Characterization of Poly–N,N'—polymethylenebisdichloromaleimides, *Journal of Polymer Science*, vol. 8, 1939–1948 (1970).

N. Boens, F.D. DeSchryver, and G. Smets, "Solid–State Ultraviolet Irradiation of Some Maleimides and Bismaleimides," *Journal of Polymer Science*, vol. 13, 201–213 (1975).

H. Zorr and H. Heusinger, "Intermediates of Radiation–Induced Polymerisation of Meleimides Studied by ESR," *European Polymer J.*, 14, 89 (1978).

M. Yamada et al., *J. Polym. Sci.*, Part B, 6, 883–888 (1968).

F.C. DeSchryver et al., *J. Am. Chem. Soc.*, 96, 6463:6469 (1974).

K. Meier et al., *J. Photochem.*, 35, 353–366 (1986).

Shimose, et al., *Polymer Preprints*, vol. 36, 1 (1995), pp. 485–486.

(List continued on next page.)

*Primary Examiner*—Susan W. Berman
*Attorney, Agent, or Firm*—Alston & Bird LLP

[57] ABSTRACT

Aliphatic maleimides and methods using the same are disclosed. Polymerization of compositions which include the compounds of the invention may be activated by irradiating the composition with radiation in the absence of a photoinitiator.

14 Claims, 10 Drawing Sheets

OTHER PUBLICATIONS

Hoyle, et al., *Academic Day Proceedings Radtech Europe '97*, pp. 115–120.

Jönsson et al., *PMSE Preprints*, 74, 319–320, (1996).

Decker et al., *Polym. Mater. Sci. Eng.*, 75, 198–349, (1996).

Clark et al., *Polym. Prep.*, 37(2), 348–349 (1996).

Jönsson et al., *Proceedings vol. I, Radtech North America '96*, 377–92, Nashvill, TN (1996).

Jönsson et al., *Nuclear Instruments and Methods in Physics Research B*, 131, 276–290 (1997).

POLYMERIZATION PROCESSES USING ALIPHATIC MALEIMIDES

CROSS-REFERENCE TO RELATED APPLICATIONS

This application is related to commonly owned copending Provisional Application Ser. No. 60/024,546, filed Aug. 23, 1996, and claims the benefit of its earlier filing date under 35 U.S.C. 119(e).

FIELD OF THE INVENTION

This invention relates generally to maleimide compounds and methods of using the same as photoinitiators in photoactivatable polymerization systems.

BACKGROUND OF THE INVENTION

Ethylenically unsaturated compounds, such as acrylate derivatives, can be polymerized by exposure to radiation, typically ultraviolet light, in the presence of a photoinitiating system. Typically, the photoinitiating system includes (1) a compound capable of initiating polymerization of the ethylenically unsaturated compound upon exposure to radiation (a "photoinitiator") and optionally (2) a coinitiator or synergist, that is, a molecule which serves as a hydrogen atom donor. The coinitiators or synergists are typically alcohols, tertiary amines, amides, or ethers which have labile hydrogens attached to a carbon adjacent to a heteroatom.

Numerous photoinitiators with varying structures are commercially available for use in different systems. However, nearly all commercially available radiation curing processes require an initiator incorporated into the formulation, a large percent of which is not consumed. The use of conventional photoinitiators typically results in the production of small molecule photo-byproducts. The presence of the residual photo-active compounds and extractables can result degradation of the physical properties of the article, such as decreased light fastness, discoloration, and lower resistance to oxidative degradation. In addition, the residual photoinitiator can be extracted or leach out of the cured article or migrate to the surface of the article, which is undesirable in many applications.

Increasingly stringent environmental protection legislation has prompted the exploration and use of formulations which contain little or no volatile organic compounds (typically solvents). Thus the use of formulations with close to 100% reactive component is of great interest.

SUMMARY OF THE INVENTION

The present invention is directed to processes for radiation curing of photopolymerizable compounds using maleimides capable of initiating photopolymerization of radiation curable compounds, in place of conventional photoinitiators. In contrast to conventional photoinitiators, substantially all of the maleimide is consumed during initiation and photopolymerization. Thus, the processes of the invention can eliminate the problems associated with residual photoinitiator in the cured product, which are often observed when using conventional photoinitiators. The use of maleimides in accordance with the invention can also minimize the need for solvent based systems.

The maleimides can be useful as photoinitiators in the photopolymerization of ethylenically unsaturated compounds, and in particular, acrylate derivatives. The maleimides can also be useful as comonomers with polymerizable compounds.

Maleimides useful in the processes of the invention include at least one maleimide unit substituted at the nitrogen atom with a functionalized aliphatic radical. Exemplary maleimide compounds include maleimides of the formula (I) below:

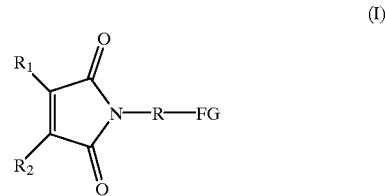

(I)

wherein:
(a) each $R_1$ and $R_2$ is independently selected from the group consisting of hydrogen, linear or branched C1 to C4 alkyl, and halogen;
(b) R is linear or branched C1 to C10 alkyl, heteroatom; or silicon-containing; and
(c1) when R is C1 to C10 alkyl, FG is a functional group selected from the group consisting of —$OR_3$, —$SR_3$, —$SiR_3$, —$OC(O)N(R_3)_2$, —$OC(O)C(=CHR_3)R_3$, —$OC(O)R_3$, —$C(O)R_3$, —$N(R_3)_2$, —$C(O)OR_3$, —NCO, —$C(O)N(R_3)_2$, —$OC(O)OR_3$, —CN, halogen, —$CH_2$N-aryl-FG, —$CH_2$N-aryl-$R_3$-FG, sulfonic acid, quaternary ammonium, and salts thereof, with the proviso that when FG is —$OR_3$, R is C1 to C4 linear or branched alkyl, and further in which each $R_3$ is selected from the group consisting of hydrogen, alkyl, aryl, cycloalkyl, arylalkyl, and alkylaryl, or
(c2) when R is a heteroatom or silicon, FG is selected from the group consisting of hydrogen, alkyl, aryl, cycloalkyl, alkylaryl, arylalkyl, alkyl-FG', and aryl-FG', wherein FG' is the same as FG as defined in (c1) above, or
(c3) FG is a functional group as defined in (c1) in combination with a spacer group linking said maleimide unit with at least one other maleimide unit to form a di- or multifunctional maleimide compound The present invention also provides novel maleimides and photopolymerizable compositions which include maleimide compounds comprising at least one maleimide unit of Formula (I) above as a component thereof.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF THE INVENTION

Figure 1:
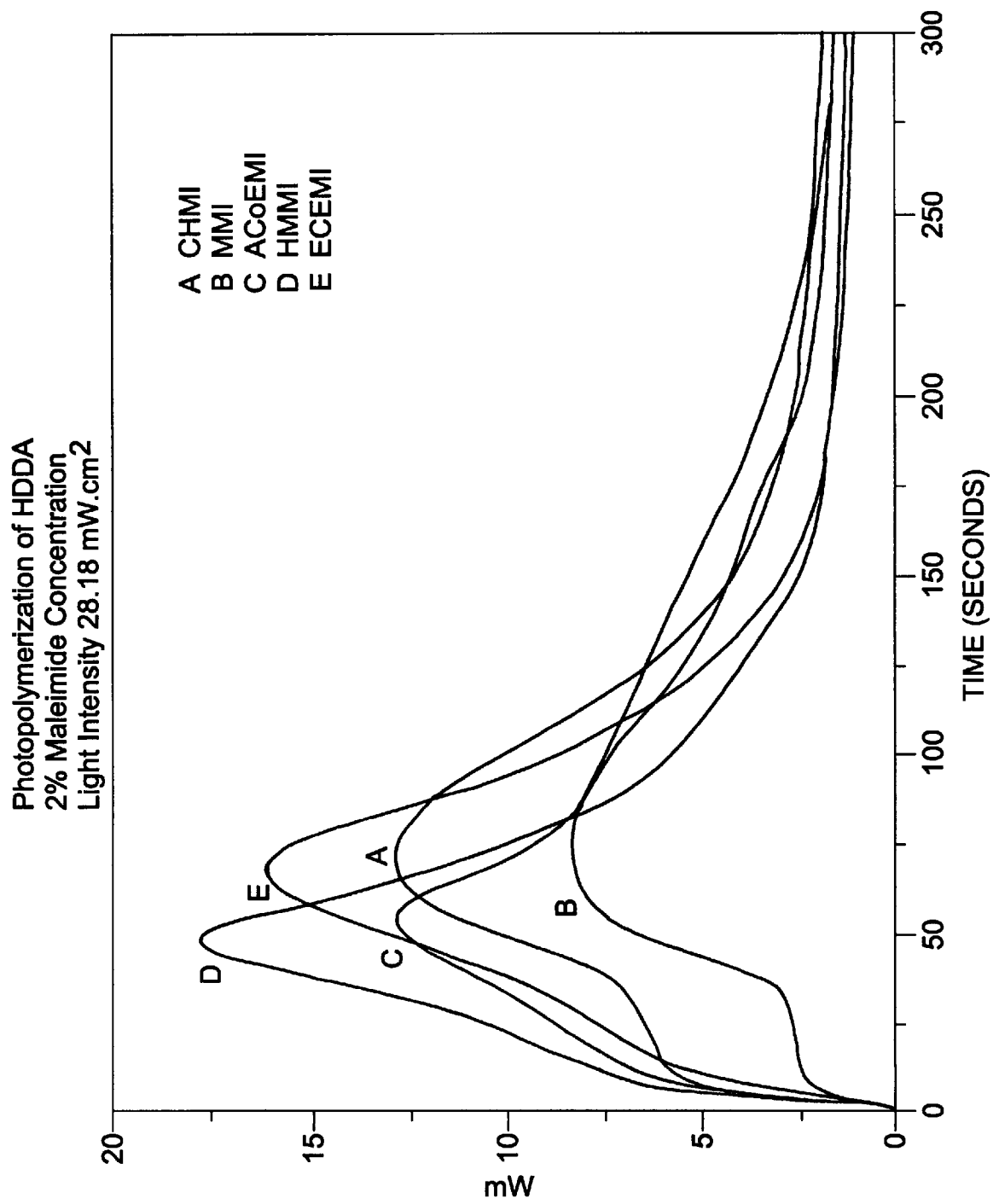
FIGS. 1–4 are graphs illustrating photopolymerization of HDDA with varying levels of aliphatic maleimides.
Figure 2:
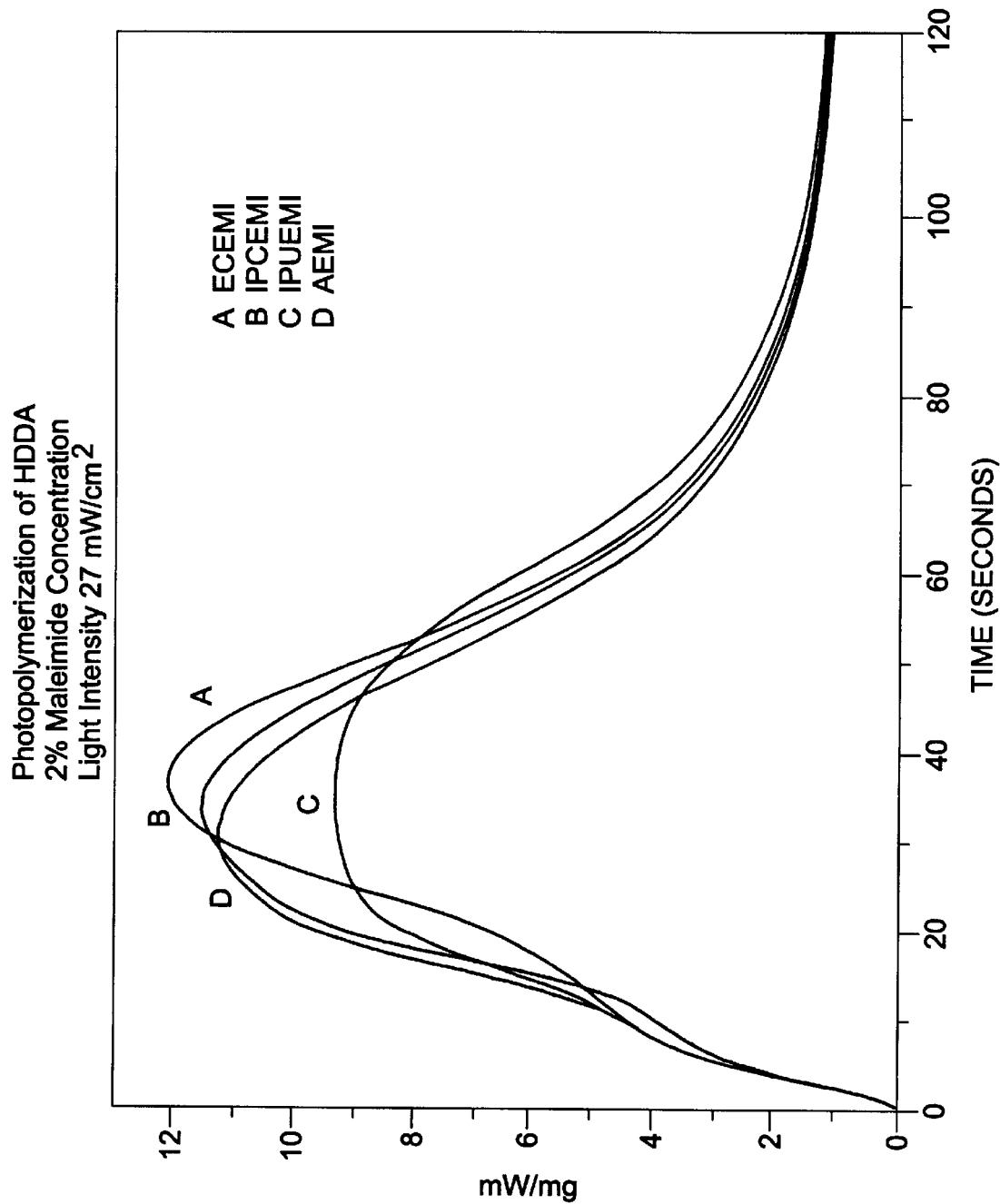
Figure 3:
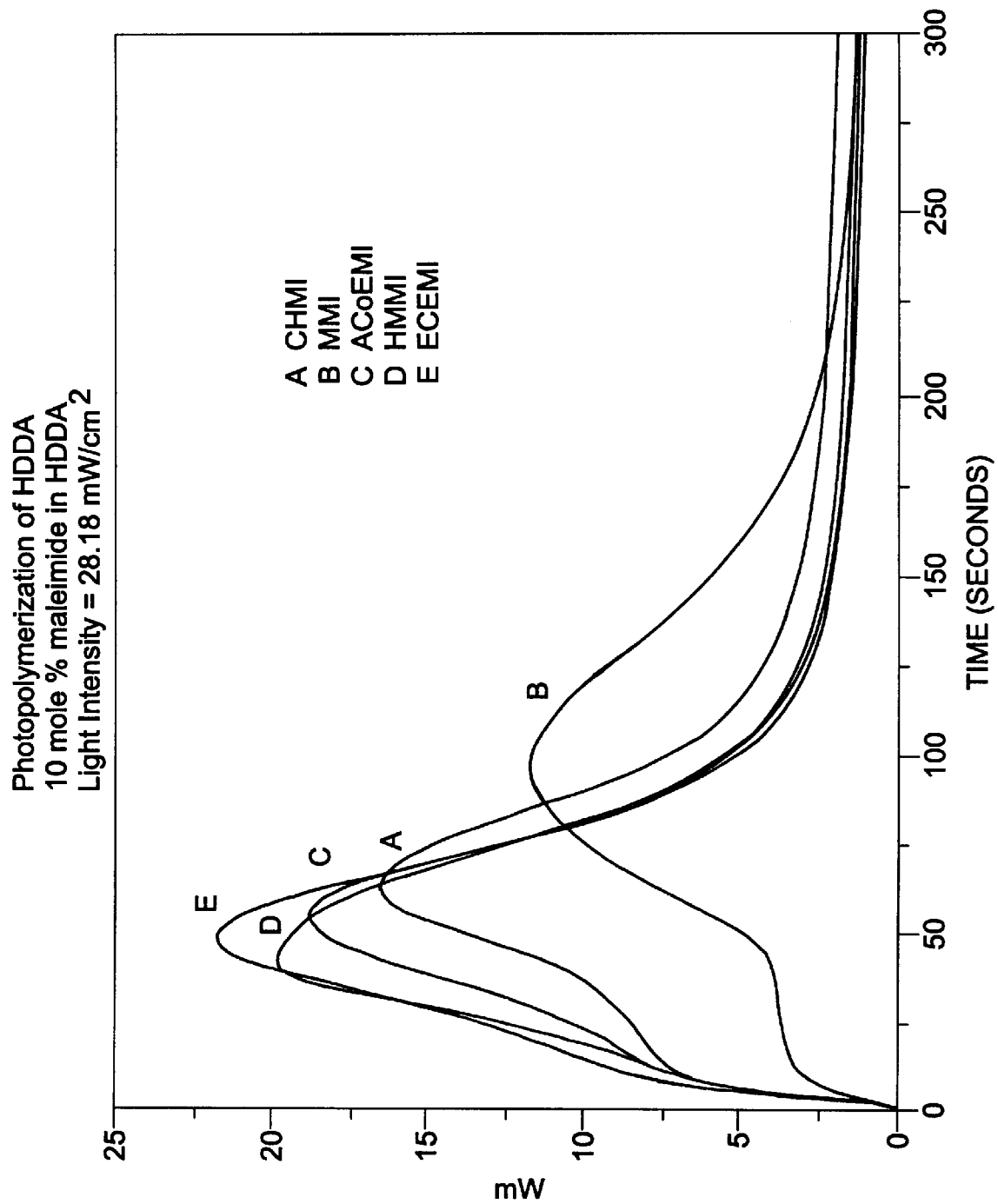
Figure 4:
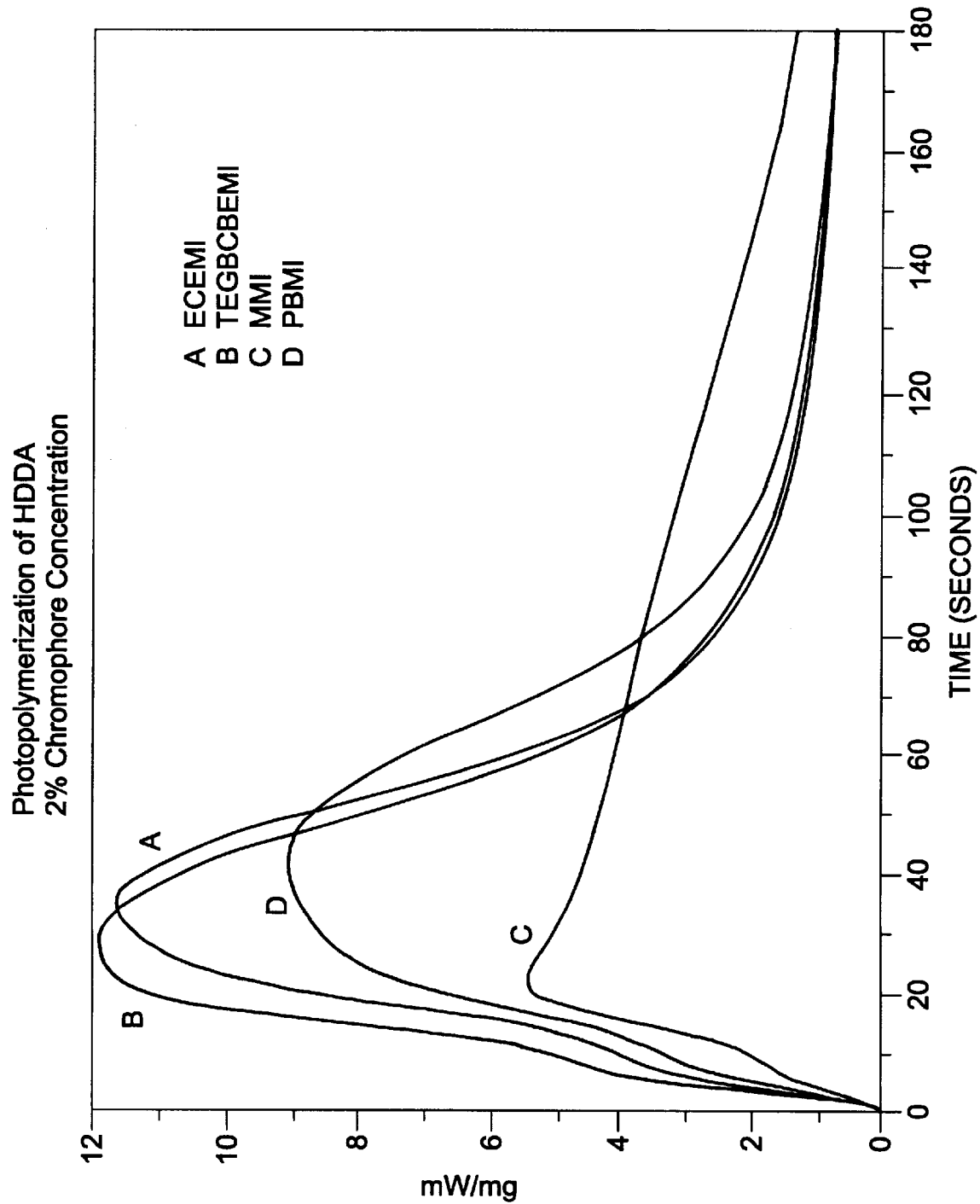
Figure 5:
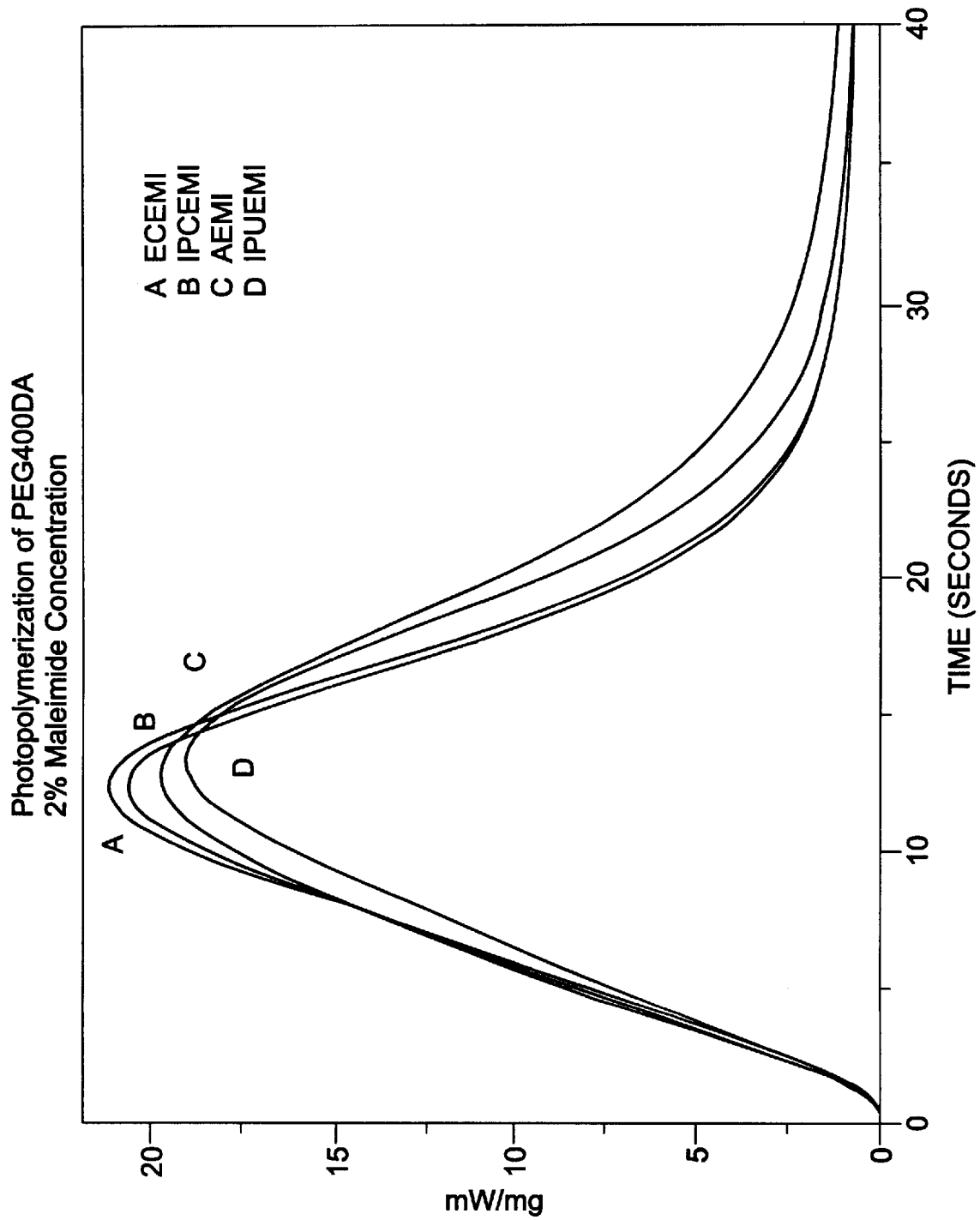
FIGS. 5–9 are graphs illustrating photopolymerization of PEG400DA with varying levels of aliphatic maleimides.
Figure 6:
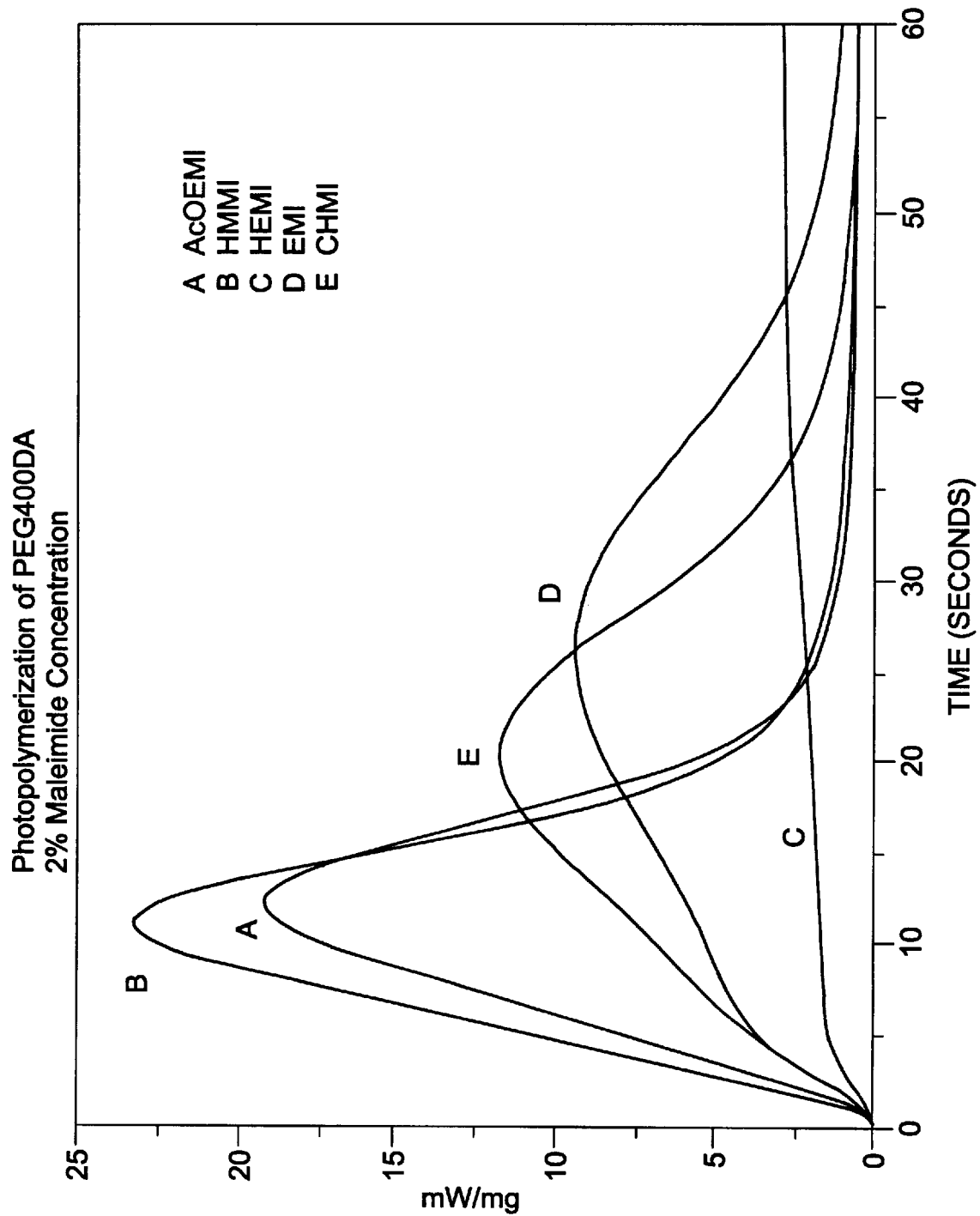
Figure 7:
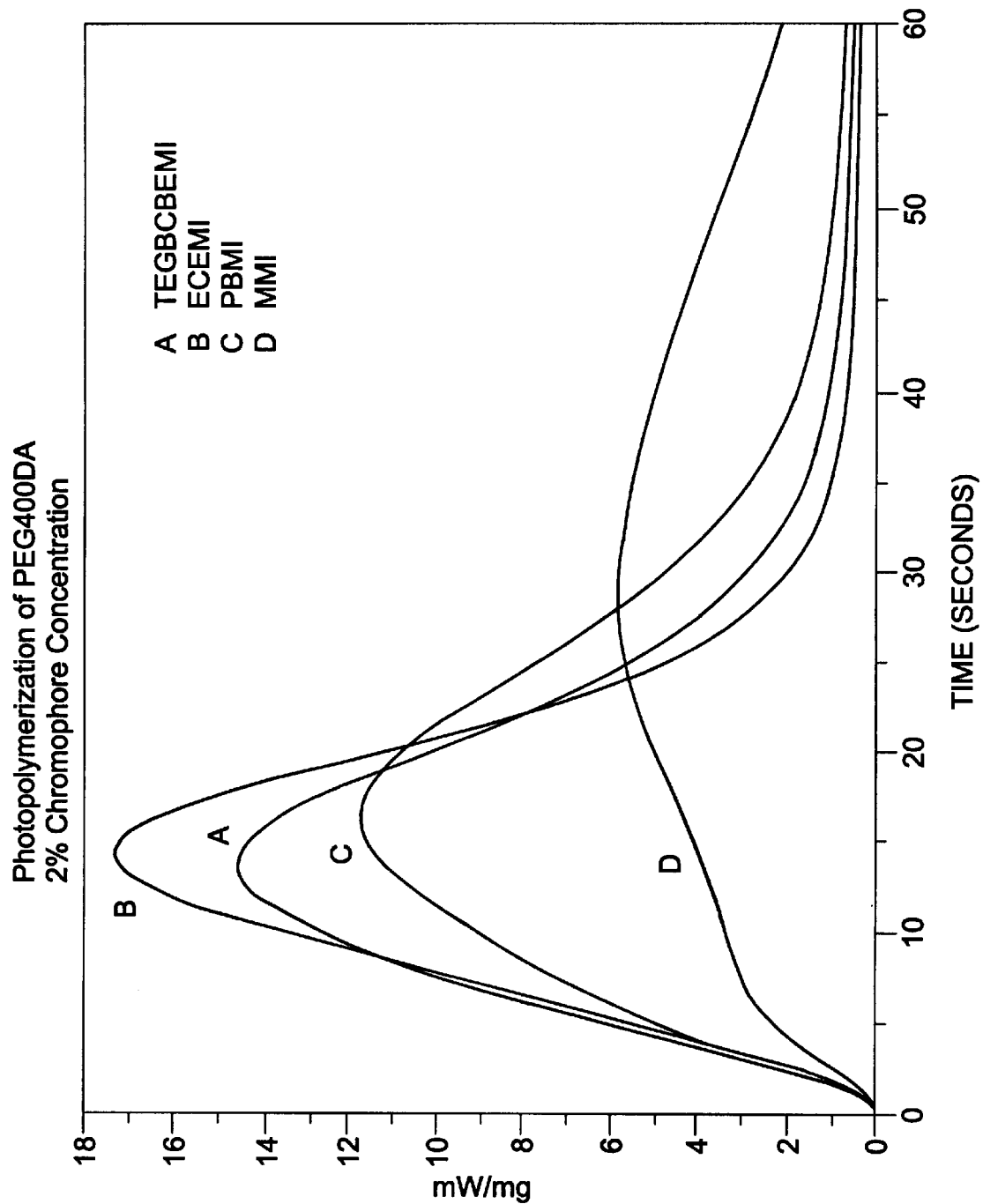
Figure 8:
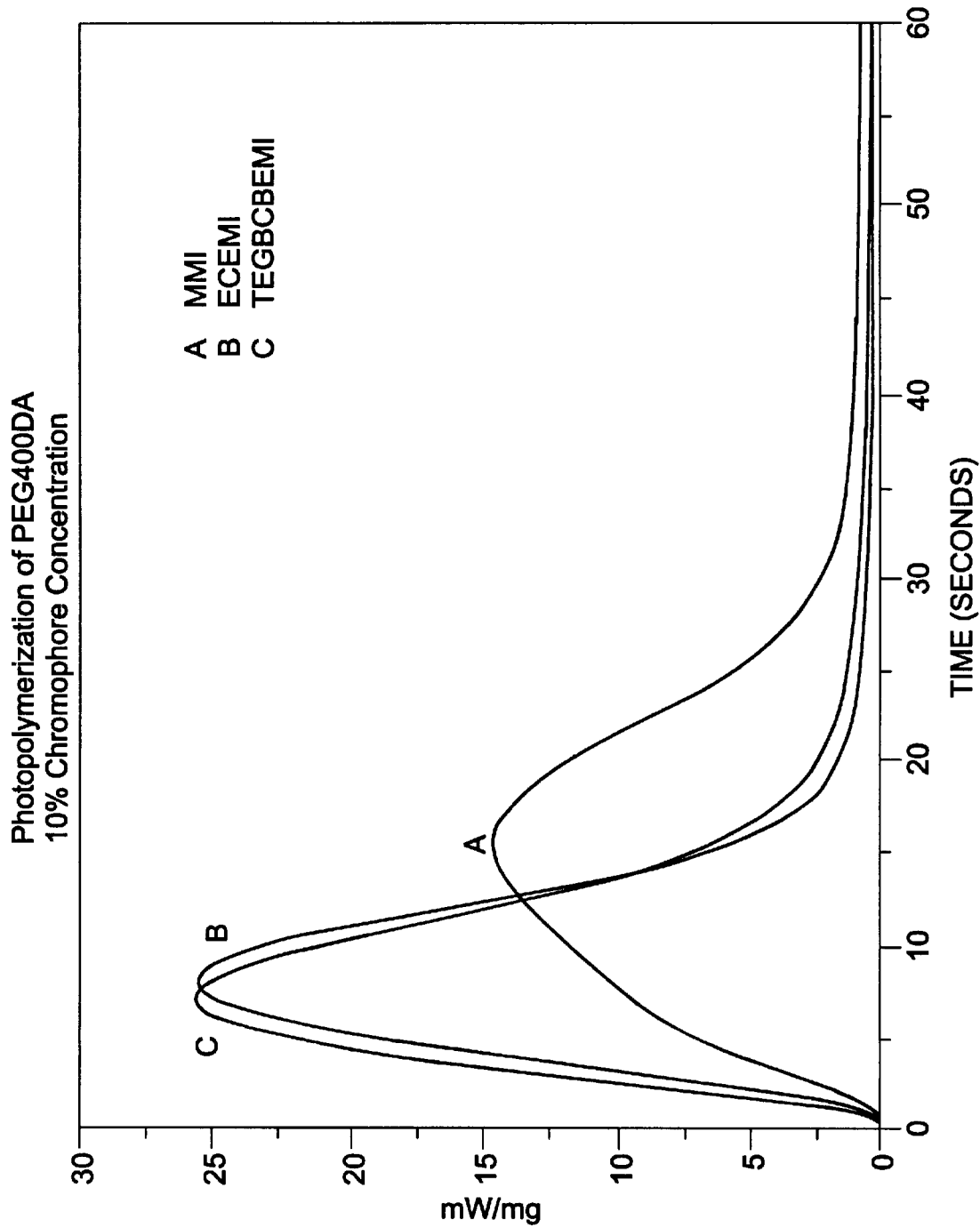

Aliphatic maleimide compounds useful in the invention include compounds having at least one maleimide unit substituted with a functionalized aliphatic radical at the nitrogen atom. The aliphatic radical preferably is a linear or branched C1 to C10 alkyl, and more preferably methyl or ethyl. The alkyl is optionally substituted with C1 to C4 alkyl, C1 to C4 alkoxy, halogen, and the like as described below.

The maleimide compound can be monofunctional (have one maleimide functional group), or can be di- or multi-functional (have two or more maleimide functional groups). For example, two or more aliphatic maleimide units can be connected or coupled via a spacer group(s), such as, but not limited to, linear or branched C1 to C10 alkyl, C3 to C6 cycloalkyl optionally substituted with C1 to C4 alkyl, C1 to C10 oxyalkyl, which can include one or more oxygen atoms, such as that derived from ethylene glycol, carbonate, and the like. Still further, maleimide compounds useful in the invention include maleimide units connected to polymeric or oligomeric compounds (typically having a molecular weight of at least about 1000)

Exemplary maleimide compounds can have the formula (I) below:

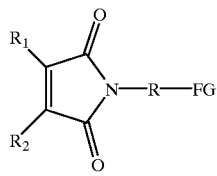

wherein:
(a) each $R_1$ and $R_2$ is independently selected from the group consisting of hydrogen, linear or branched C1 to C4 alkyl, and halogen;
(b) R is linear or branched C1 to C10 alkyl, heteroatom; or silicon-containing; and
(c1) when R is C1 to C10 alkyl, FG is a functional group selected from the group consisting of —$OR_3$, —$SR_3$, —$SiR_3$, —$OC(O)N(R_3)_2$, —$OC(O)C(=CHR_3)R_3$, —$OC(O)R_3$, —$C(O)R_3$, —$N(R_3)_2$, —$C(O)OR_3$, —NCO, —$C(O)N(R_3)_2$, —$OC(O)OR_3$, —CN, halogen, —$CH_2$N-aryl-FG, —$CH_2$N-aryl-$R_3$-FG, sulfonic acid, quaternary ammonium, and salts thereof, in which each $R_3$ is selected from the group consisting of hydrogen, alkyl, aryl, cycloalkyl, arylalkyl, and alkylaryl, or
(c2) when R is a heteratom or silicon, FG is selected from the group consisting of hydrogen, alkyl, aryl, cycloalkyl, alkylaryl, arylalkyl, alkyl-FG', and aryl-FG', wherein FG' is the same as FG as defined in (c1) above, or
(c3) FG is a functional group as defined in (c1) in combination with a spacer group linking said maleimide unit with at least one other maleimide unit to form a di- or multifunctional maleimide compound. Exemplary spacer groups include without limitation linear or branched C1 to C10 alkyl, C3 to C6 cycloalkyl, optionally substituted with lower C1 to C4 alkyl, C1 to C10 oxyalkyl, which can include one or more oxygen atoms, such as that derived from ethylene glycol, carbonate, and the like.

As used herein, the term *alkyl* refers to linear or branched C1 to C10 alkyl, such as but not limited to methyl, ethyl, propyl, butyl, isopropyl, and the like, optionally substituted with halogen, aryl, arylalkyl, alkylaryl, cycloalkyl, alkoxy, heteroatoms, silicon, and the like. The term cycloalkyl refers to C3 to C6 cycloalkyl, such as but not limited to cyclopentyl and cyclohexyl, also optionally substituted with halogen, aryl, alkyl, arylalkyl, alkylaryl, alkoxy, heteroatoms, silicon and the like. The term *aryl* refers to C3 to C10 cyclic aromatic groups such as but not limited to phenyl, naphthyl, and the like, optionally substitututed with halogen, alkyl, arylalkyl, alkylaryl, cycloalkyl, alkoxy, heteratoms, silicon, and the like. The term *heteroatom* refers to oxygen, sulfur, and nitrogen.

Exemplary maleimides useful in the process of the invention include, but are not limited to, hydroxy methylmaleimide (HMMI)(Ia)

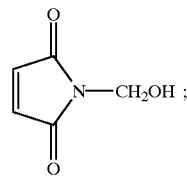

hydroxy ethylmaleimide (HEMI) (Ib)

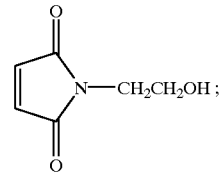

triethylene glycol biscarbonate bisethylmaleimide (TEGBCBEMI) (Ic)

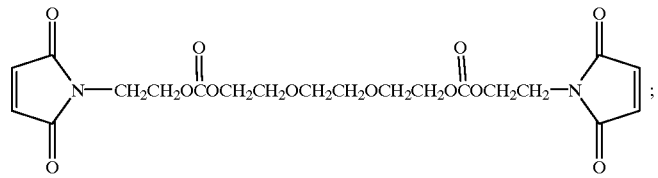

2-ethylcarbonate ethylmaleimide (2ECEMI) (Id)

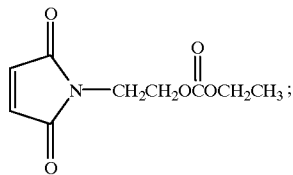

2-isopropyl urethane ethylmaleimide (2IPUEMI) (Ie)

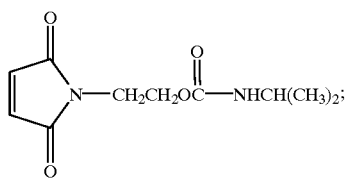

2-acryloyl ethylmaleimide (2AEMI) (If)

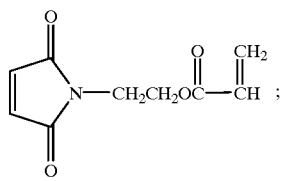

acetoxy ethyl maleimide (AcOEMI) (Ig)

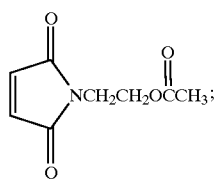

isophorone bisurethane bisethylmaleimide (IPBUBEMI) (Ih)

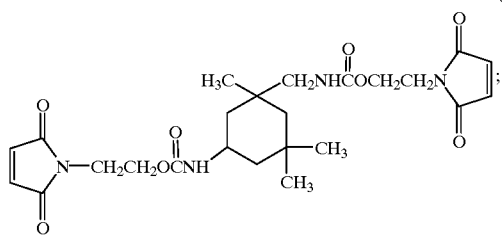

bisethylmaleimide carbonate (BEMIC) (Ii)

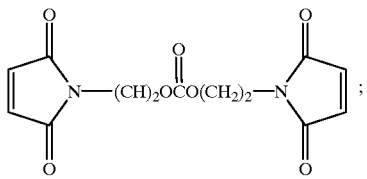

4,9-Dioxa-1,12 Dodecane Bismaleimide (4,9-DO-1,12-DDBMI) (Ij)

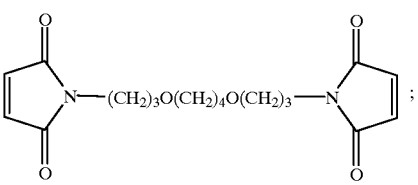

and the like.

Generally, maleimides compounds which include at least one maleimide unit of Formula (I) can be prepared using techniques known in the art. See, for example, Z. Y. Wang, Synthetic Comm. 20(11) 1607–1610 (1990); P. O. Tawney et al., J. Org. Chem. 26, 15 (1961); and U.S. Pat. No. 2,542,145.

The present invention also provides photopolymerizable compositions which include an aliphatic maleimide as a component thereof, for example, as a photoinitiator, a comonomer, and the like. As used herein, and as will be appreciated by the skilled artisan, the term photopolymerizable composition refers to compositions which harden or cure upon exposure to radiation.

Generally the compositions of the invention include ethylenically unsaturated compounds, including monomers and oligomers derived from acrylic and methacrylic acid, optionally dispersed or dissolved in a suitable solvent that is copolymerizable therewith, and mixtures thereof, which are photopolymerizable when exposed to a source of radiation (ultraviolet or UV radiation, or radiation outside the UV spectrum), particularly free radical polymerizable systems. As will be appreciated by the skilled artisan, the photopolymerizable compounds can be monofunctional, or can include two or more polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitrites. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, vinyl and vinylidene esters, vinyl and vinylidene ethers, vinyl and vinylidene ketones, butadiene, vinyl aromatics, i.e., styrene, alkyl styrenes, halostyrenes, alkoxystyrenes, divinyl benzenes, vinyl toluene, and the like are also included. Prepolymers include acrylated epoxides, polyesters and polyurethanes, and are typically combined with a suitable monomer for viscosity control.

The photopolymerizable compounds may be polymerized to form homopolymers or copolymerized with various other monomers.

The photopolymerizable compound can be present in the compositions of the invention in amounts from about 99.99 to about zero percent by weight based on the total weight of the composition.

The maleimides compounds which include at least one maleimide unit of Formula (I) can be used singly or as a mixture thereof, and are useful as photopolymerization initiators. In this aspect of the invention, the maleimide compounds can be present in the photopolymerizable composition in an amount sufficient to initiate polymerization thereof upon exposure to radiation. The composition can include about 0.01 to about 100 percent by weight maleimide compound, based on the total weight of the photopolymerizable compounds. The maleimides are particularly advantageous for use in "photoinitiator-free" systems, in which the maleimide(s) replace conventional photoinitiators. Although not wishing to be bound by any explanation of the invention, it is believed that the aliphatic maleimides can initiate polymerization via hydrogen abstraction mechanisms.

The photopolymerizable compositions of the invention may also contain other conventional agents, such as polymerization inhibitors, fillers, ultraviolet absorbers and organic peroxides. It can also be advantageous to also include as a component of the compositions of the invention a coinitiator or synergist, that is, a molecule which serves as a hydrogen atom donor or an electron donor. Coinitiators or synergists are known in the art, and are typically alcohols, tertiary amines or ethers which have available hydrogens attached to a carbon adjacent to a heteroatom. Such coinitiators are typically present in an amount between about 0.2 and about 25 percent by weight based on the total weight of the composition. Suitable compounds include, but are not limited to, triethanolamine, methyl-diethanolamine, ethyldiethanolamine and esters of dimethylamino benzoic acid. Other known coinitiators or accelerators can also be used. These compounds behave as coinitiators or accelerators for the primary photoinitiators and can increase the efficiency and speed of the polymerization process.

The photopolymerizable compositions can be applied or deposited on a surface of a substrate using conventional techniques and apparatus. The composition can be applied as a substantially continuous film. Alternatively, the composition can be applied in a discontinuous pattern. The thickness of the deposited composition can vary, depending upon the desired thickness of the resultant cured product. One advantage of the invention is that relatively thick coatings of polymerizable compositions. For example, the inventors have found that PEG400DA comprising 2 to 10% by mole ECMI or 2AEMI can be effective for a 1.5 to 7 cm thick or bulk composition using a medium pressure mercury lamp (30 mW/cm).

Typically, the substrate is coated with the uncured photopolymerizable composition and passed under a commercially available UV or excimer lamp on a conveyer moving at predetermined speeds. The substrate to be coated can be, for example, metal, wood, mineral, glass, paper, plastic, fabric, ceramic, and the like.

The active energy beams used in accordance with the present invention may be visible light or ultraviolet light or may contain in their spectra both visible and ultraviolet light. The polymerization may be activated by irradiating the composition with ultraviolet light using any of the techniques known in the art for providing ultraviolet radiation, i.e., in the range of 200 nm and 450 nm ultraviolet radiation, and especially with the 308 nm emission from xenon chloride exciter lamps, commercially available from Fusion Systems, or by irradiating the composition with radiation outside of the ultraviolet spectrum. The radiation may be natural or artificial, monochromatic or polychromatic, incoherent or coherent and should be sufficiently intense to activate the photoinitiators of the invention and thus the polymerization. Conventional radiation sources include fluorescent lamps, excimer lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention.

The compositions are useful in any of the types of applications known in the art for photopolymerizations, including as a binder for solids to yield a cured product in the nature of a paint, varnish, enamel, lacquer, stain or ink. The compositions can also be useful in the production of photopolymerizable surface coatings in printing processes, such as lithographic printing, screen printing, and the like. The compositions can also be useful in applications in which the compositions are applied to articles which are to be exposed to the environment, such as signage. Radiation cured coatings produced using conventional photoinitators typically degrade over time (as evidenced by yellowing, increasing brittleness, and the like), which degradation is exacerbated by direct exposure to sunlight. In contrast, radiation cured coatings prepared using the maleimide compounds can exhibit minimal degradation over time, even when exposed to direct sunlight. The maleimides can also be water soluble.

The present invention will be further illustrated by the following non-limiting examples.

EXAMPLE 1

Synthesis of Hydroxy Methylmaleimide (HMMI)

Maleimide (10 g, 0.103 mol) was added to 10 mL of a 37% solution of formaldehyde and 0.31 mL of a 5% solution of NaOH was added. Within 10 minutes all of the maleimide had dissolved and an exothermic reaction proceeded. The solution was stirred for 2 hours where white crystals were observed. The solution was placed in a freezer overnight and the resulting crystals filtered and washed with ice cold ethanol and diethyl ether. The white crystals were purified twice by sublimation. See P. O. Tawney, R. H. Snyder, R. P. Conger, K. A. Leibbrand, C. H. Stiteler, and A. R. Williams *J. Org. Chem.* 26, 15 (1961).m.p. 104–106° C. (9.77 g, 74.6%). $^1$H-NMR (Acetone-$d_6$, δ, ppm): 4.96 (2H, —CH$_2$—, s), 5.33 (1H, —OH, s), 6.93 (2H, —CH=CH—, s). $^{13}$C—NMR (Acetone-$d_6$, δ, ppm): 60.9 (1C, —CH$_2$—), 135.6 (2C, —CH=CH—), 173.1 (1C, —C=O).

EXAMPLE 2

Synthesis of Hydroxy Ethylmaleimide (HEMI)

Ethanolamine (80.96 g, 1.32 mol) was added to 500 mL of ethanol and cooled to 0° C. using an ice bath. 3,6-Endoxo-1,2,3,6-tetrahydrophthalic anhydride (220.21 g, 1.32 mol) was added to the solution and allowed to stir overnight. The yellow tinted crystals were used without purification. The solution was refluxed for four hours with azeotropic removal of water. The solution was cooled to 0° C. and the resulting crystals filtered (151.74 g, 54.95%). Removal of furan was facilitated by refluxing the crystals in xylenes for 4 hours with quantitative yield of hydroxy ethylmaleimide after purification by sublimation to yield white crystals, —CH$_2$O—), 134.2 (2C, —CH=CH—), 171.2 (2C, —NC=O m.p. 68° C. $^1$H-NMR (CDCl$_3$, δ, ppm): 2.62 (1H, —OH, s), 3.82–3.77 (4H, —NCH$_2$CH$_2$O—, overlapping), 6.76 (2H, —CH=CH—, s). $^{13}$C-NMR (CDCl$_3$, δ, ppm): 40.5 (1C, —NCH$_2$—), 60.5 (1C,).

EXAMPLE 3

Triethylene Glycol Biscarbonate Bisethylmaleimide (TEGBCBEMI)

HEMI (25.65 g, 0.182 moles) and pyridine (14.38 g, 0.182 moles) were dissolved in THF (130 mL) and the solution was stirred at room temperature. Triethylene glycol bischloroformate (25.0 g, 0.091 moles) was added dropwise and stirred for 90 minutes. The pyridine salt was filtered off and the solution was combined with 200 mL of a 1N HCl solution. The product was extracted with methylene chloride and washed with a 1N HCl solution followed by water and then dried over magnesium sulfate. The red solution was diluted to a volume of 150 mL and purified by column chromatography (2.5 cm×21 cm) using silica gel as the packing and methylene chloride as the mobile phase yielding white crystals, m.p. 65° C. (26.75 g, 60.76%). $^1$H-NMR (CDCl$_3$), δ, ppm): 3.64–3.68 (4Hφ—OCH$_2$—, t), 3.69–3.74 (4H, ε—OCH$_2$—, t), 3.81–3.86 (4H, —NCH$_2$—, t), 4.26–4.3 (8H, —CH$_2$O(C=O)OCH$_2$13 , t), 6.75 (4H, —CH=CH—, s). $^{13}$C-NMR (CDCl$_3$, δ, ppm): 36.6 (2C, —NCH$_2$—), 64.7 (2C,), 67.3 (2C,), 68.8 (2C,), 70.6 (2C,), 134.4 (4C, —CH=CH—), 154.8 (2C, O(C=O)O), 170.4 (4C, —NC=O).

EXAMPLE 4

Synthesis of 2-Ethylcarbonate Ethylmaleimide (2ECEMI)

Hydroxy ethylmaleimide (29.87 g, 0.212 moles) and pyridine (16.7 g, 0.212 moles) were dissolved in THF (170 mL) and the solution was stirred at room temperature. Ethyl chloroformate (22.97 g, 0.212 moles) was added dropwise and stirred for 90 minutes. The pyridine salt was filtered off and the solution was combined with 200 mL of a 1N HCl solution. The product was extracted with methylene chloride and washed with a 1N HCl solution followed by water and then dried over magnesium sulfate. The red solution was concentrated and the red crystals purified by sublimation yielding white crystals, m.p. 52° C. (34.76 g, 77.04%). $^1$H-NMR (CDCl$_3$), δ, ppm): 1.26–1.34 (3H, —CH$_3$, t), 3.81–3.87 (2H —NCH$_2$—, t), 4.14–4.25 (2H, δ—CH$_2$OC=O, q), 4.25–4.30 (2H, β—CH$_2$O—, t), 6.74 (2H, —CH=CH—, s). $^{13}$C-NMR (CDCl$_3$, δ, ppm): 14.2 (1C, —CH$_3$), 36.8 (1C, —NCH$_2$—), 64.3 (1C, δ—CH$_2$O), 64.5 (1C, β—CH$_2$—), 134.4 (2C, —CH=CH—), 154.9 (1C, O(C=O)O), 170.4 (2C, —C=O).

EXAMPLE 5

Synthesis of 2-Isopropyl Urethane Ethylmaleimide (2IPUEMI)

Hydroxy ethylmaleimide (5 g, 35.4 mmol) was dissolved in 75 mL of methylene chloride 1 drop of dibutyl tin dilaurate catalyst was added. Isopropyl isocyanate (3.01 g, 35.4 mmol) was added dropwise and the solution was stirred for 3 hours. The solution was washed with water dried with magnesium sulfate. Concentration yielded white crystals which were further purified sublimation yielding white crystals, m.p. 117° C. (6.49 g, 81%). $^1$H-NMR (CDCl$_3$, δ, ppm): 1.11–1.14 (6H, —C(CH$_3$)$_2$, d), 3.74–3.79 (2H, —NCH$_2$—, t), 4.28–4.32 (2H, —CH$_2$O—, t), 4.44–4.53 (1H, —CH—, p), 6.72 (2H, —OC—CH=CH—CO—, s). NMR $^{13}$C-NMR (CDCl$_3$, δ, ppm): 170.5 (2C, C=O, maleimide), 155.1 (1C, C=O( urethane), 134.2 (2C, —CH=CH—), 61.7 (1C, β—CH$_2$), 43.6 (1C, —CH—), 37.4 (1C, α—CH$_2$), 22.9 (2C, —CH$_3$).

EXAMPLE 6

Synthesis of 2-Acryloyl Ethylmaleimide (2AEMI)

2-Hydroxyethyl maleimide (5 g, 35.4 mmol) and Et$_3$N (4.25 g, 43.0 mmol) was dissolved in 75 mL of methylene chloride and cooled to 0° C. Acryloyl chloride (3.20 g, 35.4 mmol) in 25 mL of methylene chloride was added dropwise over 30 minutes. The solution was stirred at room temperature for 30 minutes followed by refluxing for 1 hour. The triethylamine hydrochloride was removed by filtration and the yellow solution was concentrated. The yellow crystals were purified by sublimation yielding white crystals, m.p. 77–78° C. (5.00 g, 72.3%). $^1$H-NMR (CDCl$_3$, δ, ppm): 3.81–3.87 (2H, —NCH$_2$—, t) 4.22–4.33 (2H, —OCH$_2$—, t), 5.81–5.85 (2H, CH$_2$=CH, cis), 6.00–6.13 (1H, CH$_2$=CH—, q), 6.34–6.42 (1H CH$_2$=CH, trans), 6.73 (2H, —OC—CH=CH—CO—, s). $^{13}$C-NMR (CDCl$_3$, δ, ppm): 170.4 (2C, C=O, maleimide), 165.8 (1C, C=O, ester), 134.2 (2C, —CH=CH—), 131.45 (1C, —CH=), 127.9 (1C, CH$_2$=), 61.5 (1C, β—CH$_2$—), 36.8 (1C, α—CH$_2$—).

EXAMPLE 7

Synthesis of Acetoxy Ethyl Maleimide (AcOEMI)

Maleic anhydride (172.32 g, 1.75 mol) was added to ethanolamine (107.34 g, 1.75 mol) and dissolved in 500 mL of acetone while stirring overnight in an ice bath. To the solution, 400 mL of acetic anhydride (4.23 mol) was added with sodium acetate (144 g, 1.75 mol). The solution was heated to 80° C. and stirred for 1 hour. The contents were poured into ice water and the acetic acid neutralized with K$_2$CO$_3$. The product was extracted with methylene chloride and then dried using magnesium sulfate. The product was purified by sublimation yielding white crystals, m.p. 76° C. (44.1 g, 13.45%) $^1$H-NMR (CDCl$_3$, δ, ppm): 2.02 (3H, —CH$_3$, s), 3.82–3.77 (2H, —NCH$_2$—, t), 4.25—4.20 (2H, —CH$_2$O—, t), 6.75 (2H, —CH=CH—, s). $^{13}$C-NMR (CDCl$_3$, δ, ppm): 20.7 (1C, —CH3), 37.0 (1C, —NCH$_2$—), 61.5 (1C, —CH$_2$O—), 134.3 (2C, —CH=CH—), 170.5 (2C, —NC=O), 170.8 (1C, —OC=O).

EXAMPLE 8

Synthesis of 4,9-Dioxa-1,12 Dodecane Bismaleimide (4,9-DO-1,12-DDBMI)

4,9-Dioxa-1,12-dodecane diamine (25 g, 0.122 mol) was dissolved in acetone and added dropwise to a solution of maleic anhydride (24 g 0.244 mol) in 120 mL of acetone under cooling using an ice bath in a nitrogen atmosphere. The solution was stirred overnight and the contents were then poured into water and the bismaleamic acid filtered and washed with ethanol and diethylether.

The bismaleamic acid (29.96 g, 74.8 mmol) was dissolved in an acetone 120 mL and triethylamine (41.7 mL, 0.300 mol) solution. The solution was heated to reflux, where acetic anhydride (21.2 mL, 0.224 mol) was added dropwise, the solution was refluxed for 12 hours. The solution was added to ice water and the precipitate filtered and dried. The sample was purified by column chromatography using silica gel as the adsorbent and methylene chloride as the mobile phase yielding white crystals, m.p. 65° C. (5.5 g, 20.2%). $^1$H-NMR (CDCl$_3$, δ, ppm): 1.60–1.54 (2H, ε—CH$_2$—), 1.91–1.78 (2H, β—CH$_2$—), 3.44–3.28 (4H, —CH$_2$OCH$_2$—), 3.66–3.59 (2H, —NCH$_2$—, t), 6.70 (2H, —CH═CH—, s). $^{13}$C-NMR (CDCl$_3$, δ, ppm): 26.4 (2C, ε—CH$_2$—), 28.6 (2C, β—CH$_2$—), 35.6 (2C, —NCH$_2$—), 68.2, 70.7 (4C, —CH$_2$OCH$_2$—), 134.2 (2C, —CH═CH—), 170.8 (2C, —NC═O).

EXAMPLE 9

Synthesis of Isophorone bisurethane bisethylmaleimide (IPBUBEMI)

Hydroxy ethylmaleimide (10 g, 0.141 mol) was dissolved in acetone and purged with nitrogen while stirring in an ice bath. One drop of dibutyl tin dilaurate was added to the solution. The isophorone diisocyanate (30.5 g, 0.141 mol) was added dropwise over 2–3 hours. The solution was allowed to stir overnight and a white precipitate was obtained after solvent removal m.p. 105–112° C. (40.5 g, 100%). $^1$H-NMR (D$_6$-DMSO, δ, ppm): 3.63–3.58 (2H, —NCH$_2$—), 4.08–4.03 (2H, —CH$_2$O—, t), 7.03 (2H, —CH═CH—, s). $^{13}$C-NMR (D$_6$-DMSO, δ, ppm): 134.5 (2C, —CH═CH—), 154.9 (2C, NHC═O), (170.7 (2C, —NC═O).

EXAMPLE 10

Synthesis of Bispropyl Maleimide (PBMI)

Diaminopropane was dissolved in 100 mL of dimethyl acetamide (DMAC) and added dropwise to a solution of maleic anhydride in DMAC under cooling using an ice bath in a nitrogen atmosphere. The solution was stirred overnight and the contents were then poured into water and the bismaleamic acid filtered and washed with ethanol and diethylether.

The bismaleamic acid (84.54 g, 0.312 mol) was dissolved in 312 mL of an acetone and triethylamine (87 mL, 0.624 mol) solution. The solution was heated to reflux and acetic anhydride (88 mL, 0.61 mol) was added dropwise through a reflux condenser and the solution was refluxed for 12 hours. The solution was added to ice water and the precipitate filtered and dried. The sample was purified by column chromatography using silica gel as the adsorbent and methylene chloride as the mobile phase yielding white crystals, m.p. 166° C. (19.28 g, 26.3%). $^1$H-NMR (CDCl$_3$, δ, ppm): 2.00–1.86 (2H, —CH$_2$—, p), 3.57–3.50 (4H, —NCH$_2$—, t), 6.71 (2H, —CH═CH—, s). $^{13}$C-NMR (CDCl$_3$, δ, ppm): 27.3 (1C, —CH$_2$—), 35.3 (2C, —NCH$_2$—), 134.2 (2C, —CH═CH—), 170.6 (2C, —NC═O).

EXAMPLE 11

Synthesis of Bisethylmaleimide Carbonate (BEMIC)

Hydroxy ethylmaleimide (10.0 g, 70.1 mmol) was dissolved in a solution of methylene chloride (71 mL) and triethylamine (9.87 mL, 70.8 mmol) and cooled with an ice bath to 0° C. Triphosgene (3.504 g, 12 mmol) was added over a period of 4 hours and the resulting solution filtered. The supernatant was washed with 1N hydrochloric acid, 5% potassium carbonate solution and water. The solution was dried over magnesium sulfate and purified using activated carbon to yield white crystals (4.0 g, 18.5%). $^1$H-NMR (CDCl$_3$, δ, ppm): 3.82 (4H, —NCH$_2$—, t), 4.27 (2H, —CH$_2$O—, t), 6.73 (2H, —CH═CH—, s). $^{13}$C-NMR (CDCl$_3$, δ, ppm): 36.6 (2C, —NCH$_2$—), 64.9 (2C, —CH$_2$O—), 134.2 (2C, —CH═CH—), 154.5 (1C, C═O) 170.8 (2C, —NC═O).

EXAMPLE 12

Photopolymerization

Photo-DSC results (FIGS. 1–8) established that the compounds of the invention photoinitiate polymerization of hexanediol diacrylate (HDDA) and polyethylene glycol diacrylate (PEG400DA). Additional monomers and crosslinked polymers may also be photoinitiated by these compounds. The photo-DCS traces show the relative performance of the compounds of the invention in the peak heat release rate, and in the time required to reach the peak rate.

Figure 9:
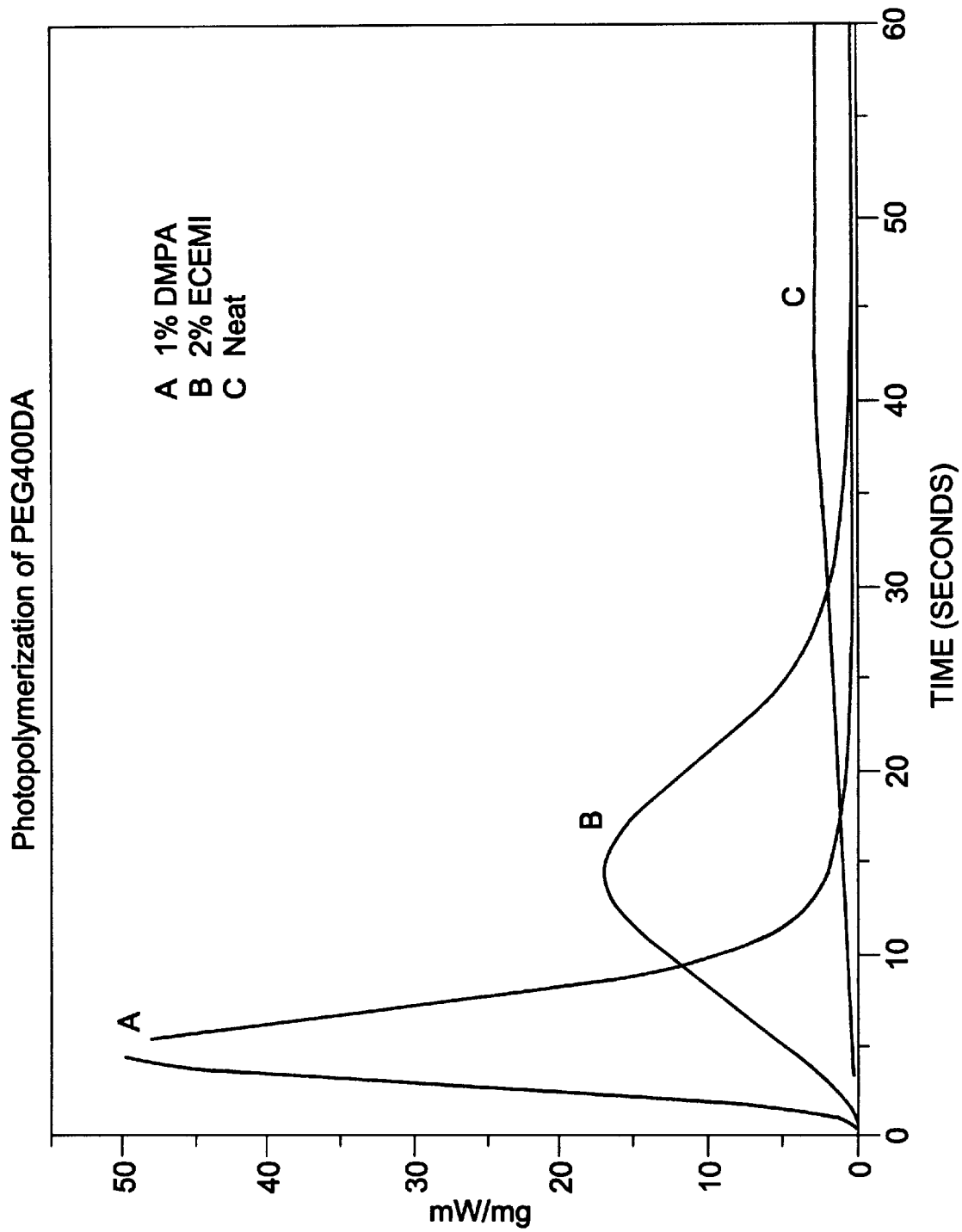

A comparative example of photopolymerization of PEG400DA with dimethoxy phenylacetophenone (DMPA) and ECEMI (FIG. 9) shows that both compounds photoinitiate.

Figure 10:
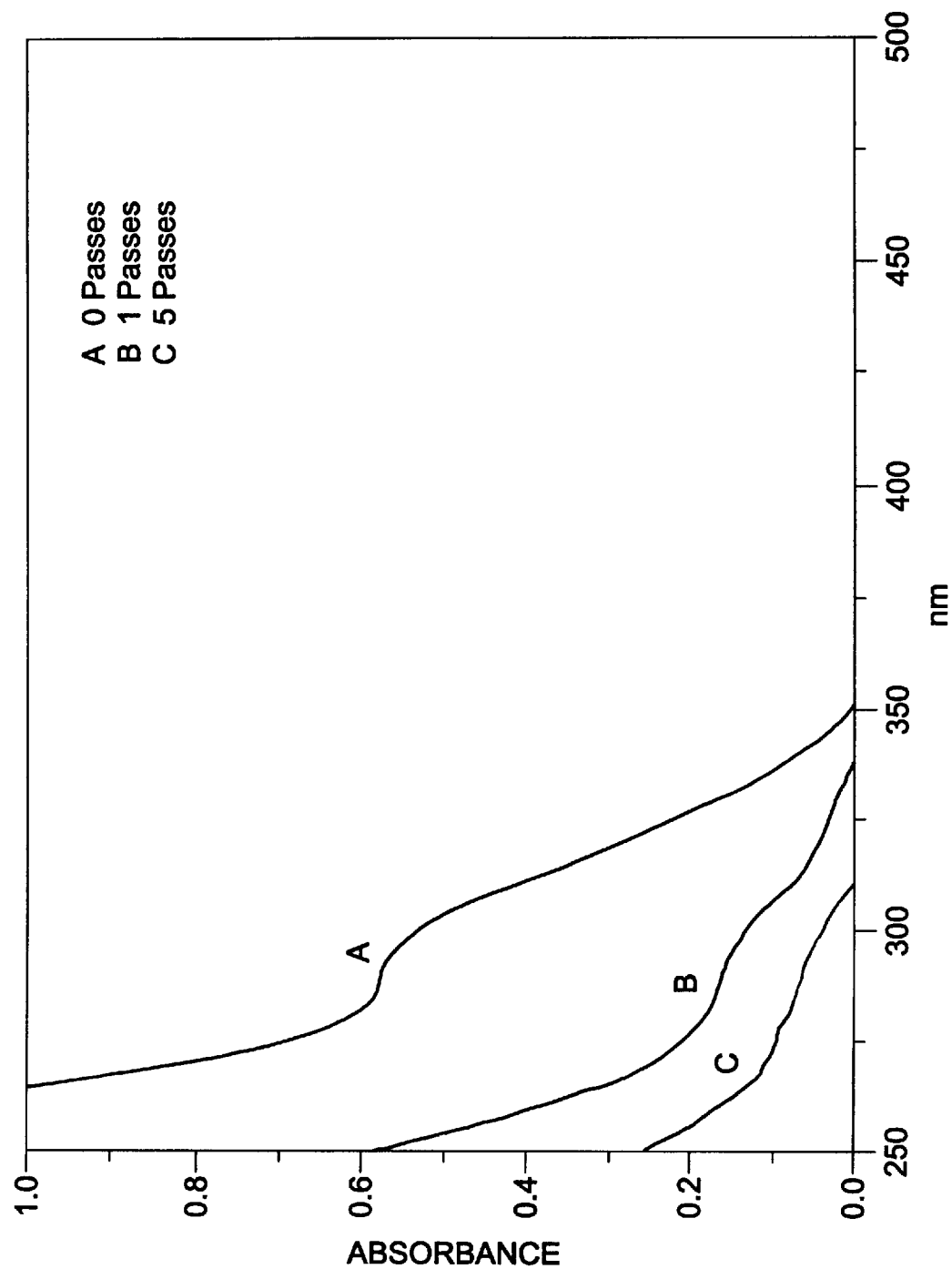
FIG. 10 is a graph illustrating the consumption of an aliphatic maleimide upon subsequent exposure to UV radiation.

UV absorbance of a formulation of 10 mole percent ECEMI in PEG400DA was measured before and after curing a 25 micron film under a Fusion H bulb at a belt speed of 80 feet per minute (FIG. 10). The characteristic absorbance of the maleimide is reduced after one pass under the lamp and is reduced further after five passes under the lamp. This establishes that the maleimide is indeed consumed and no measurable photo-byproducts are created.

The foregoing examples are illustrative of the present invention and are not to be construed as limiting thereof.

That which is claimed is:

1. A method of photopolymerizing a photopolymerizable vinyl compound having at least one ethylenically unsaturated double bond, comprising exposing photopolymerizable vinyl compound to radiation in the presence of a maleimide compound of the formula

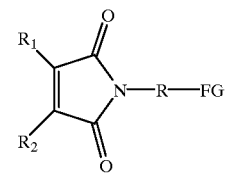

wherein:
- (a) each R$_1$ and R$_2$ is independently selected from the group consisting of hydrogen, linear or branched C1 to C4 alkyl, and halogen;
- (b) R is linear or branched C1 to C10 alkylene, oxygen, sulfur, nitrogen, or —SiH$_2$—; and
- (c1) when R is C1 to C10 alkylene, FG is a functional group selected from the group consisting of —OR$_3$, —SR$_3$, —SiH$_2$R$_3$, —OC(O)N(R$_3$)$_2$, —OC(O)C (=CHR₃)R₃, —OC(O)R₃, —C(O)R₃, —N(R₃)₂, —C(O)OR₃, —NCO, —C(O)N(R₃)₂, —OC(O)OR₃, —CN, halogen, —CH₂N-aryl-FG', —CH₂N-aryl-R₃-FG', sulfonic acid, quaternary ammonium, and salts thereof, in which each R₃ is selected from the group consisting of hydrogen, alkyl, aryl, cycloalkyl, arylalkyl, and alkylaryl, with the proviso that when R is —OR₃, then R₃ is not hydrogen, or when R is —OC(O)N(R₃)₂, then R₃ is not aryl, or when R is —OC(O)R₃, then R₃ is not alkyl, and in which FG' is selected from the group consisting of —OR₃, —SR₃, —SiH₂R₃, —OC(O)N(R₃)₂, —OC(O)C(=CHR₃)R₃, —OC(O)R₃, —C(O)R₃, —N(R₃)₂, —C(O)OR₃, —NCO, —C(O)N(R₃)₂, —OC(O)OR₃, —CN, halogen, sulfonic acid, and quaternary ammonium, or (c2) when R is oxygen, sulfur, nitrogen, or —SiH₂—, FG is selected from the group consisting of hydrogen, alkyl, aryl, cycloalkyl, alkylaryl, arylalkyl, alkyl-FG", and aryl-FG", wherein FG" is the same as FG' as defined in (c1) above, or (c3) FG is a functional group as defined in (c1) in combination with a polyethylene glycol derived spacer group linking said maleimide unit with at least one other maleimide unit to form a di- or multifunctional maleimide compound.

2. The method of claim 1, wherein said photopolymerizable vinyl compound is selected from the group consisting of monomers and oligomers derived from acrylic and methacrylic acid, optionally dispersed or dissolved in a solvent that is copolymerizable therewith.

3. The method of claim 1, wherein said photopolymerizable compound is selected from the group consisting of methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, hydroxy acrylates, glycol acrylates, allyl acrylates, epoxy acrylates, aminoplast acrylates, acrylated epoxides, acrylated polyesters, acrylated polyurethanes, and mixtures thereof.

4. The method of claim 1, wherein said maleimide compound comprises a compound of the formula:

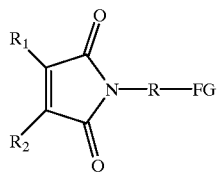

wherein R is linear or branched C1 to C10 alkylene and FG is a functional group selected from the group consisting of —OR₃, —SR₃, —SiH₂R₃, —OC(O)N(R₃)₂, —OC(O)C(=CHR₃)R₃, —OC(O)R₃, —C(O)R₃, —N(R₃)₂, —C(O)OR₃, —NCO, —C(O)N(R₃)₂, —OC(O)OR₃, —CN, halogen, —CH₂N-aryl-FG', —CH₂N-aryl-R₃-FG', sulfonic acid, quaternary ammonium, and salts thereof, in which each R₃ is selected from the group consisting of hydrogen, alkyl, aryl, cycloalkyl, arylalkyl, and alkylaryl, with the proviso that when R is —OR₃, then R₃ is not hydrogen, or when R is —OC(O)N(R₃)₂, then R₃ is not aryl, or when R is —OC(O)R₃, then R₃ is not alkyl, and in which FG' is selected from the group consisting of —OR₃, —SR₃, —SiH₂R₃, —OC(O)N(R₃)₂, —OC(O)C(=CHR₃)R₃, —OC(O)R₃, —C(O)R₃, —N(R₃)₂, —C(O)OR₃, —NCO, —C(O)N(R₃)₂, —OC(O)OR₃, —CN, halogen, sulfonic acid, and quaternary ammonium.

5. The method of claim 1, wherein said maleimide compound comprises a compound of the formula:

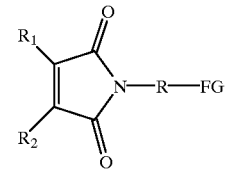

wherein R is oxygen, sulfur, nitrogen or —SiH₂— and FG is selected from the group consisting of hydrogen, alkyl, aryl, cycloalkyl, alkylaryl, arylalkyl, alkyl-FG", and aryl-FG".

6. The method of claim 1, wherein said maleimide compound comprises a compound of the formula:

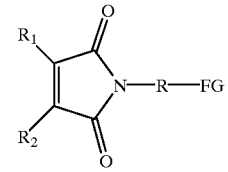

wherein R is linear or branched C1 to C10 alkylene, oxygen, sulfur, nitrogen, or —SiH₂— and FG is a functional group selected from the group consisting of —OR₃, —SR₃, —SiH₂R₃, —OC(O)N(R₃)₂, —OC(O)C(=CHR₃)R₃, —OC(O)R₃, —C(O)R₃, —N(R₃)₂, —C(O)OR₃, —NCO, —C(O)N(R₃)₂, —OC(O)OR₃, —CN, halogen, —CH₂N-aryl-FG', —CH₂N-aryl-R₃-FG', sulfonic acid, quaternary ammonium, and salts thereof in combination with a polyethylene glycol derived spacer group linking said maleimide unit with at least one other maleimide unit to form a di- or multifunctional maleimide compound.

7. The method of claim 1, wherein said compound is selected from the group consisting of:

triethylene glycol biscarbonate bisethylmaleimide (TEGBCBEMI)

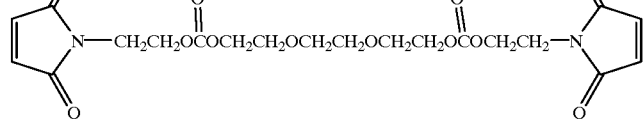

2-ethylcarbonate ethylmaleimide (2ECEMI)

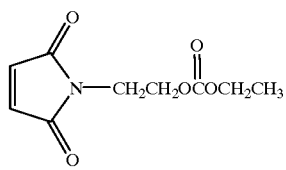

2-isopropyl urethane ethylmaleimide (2IPUEMI)

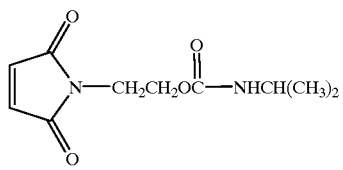

2-acryloyl ethylmaleimide (2AEMI)

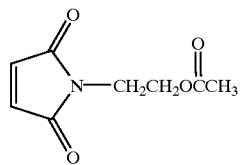

isophorone bisurethane bisethylmaleimide (IPBUBEMI)

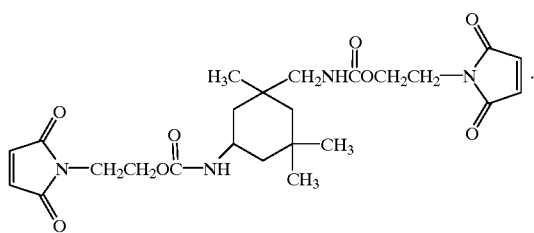

8. A photopolymerizable composition consisting essentially of a photopolymerizable vinyl compound having at least one ethylenically unsaturated double bond and at least one maleimide compound of the formula

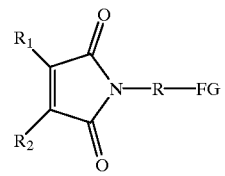

wherein:

(a) each $R_1$ and $R_2$ is independently selected from the group consisting of hydrogen, linear or branched C1 to C4 alkyl, and halogen;

(b) R is linear or branched C1 to c10 alkylene, oxygen, sulfur, nitrogen, or —SiH$_2$—; and (c1) when R is C1 to C10 alkylene, FG is a functional group selected from the group consisting of —OR$_3$, —SR$_3$, —SiH$_2$R$_3$, —OC(O)N(R$_3$)$_2$, —OC(O)C(=CHR$_3$)R$_3$, —OC(O)R$_3$, —C(O)R$_3$, —N(R$_3$)$_2$, —C(O)OR$_3$, —NCO, —C(O)N(R$_3$)$_2$, —OC(O)OR$_3$, —CN, halogen, —CH$_2$N-aryl-FG', —CH$_2$N-aryl-R$_3$-FG', sulfonic acid, quaternary ammonium, and salts thereof, in which each R$_3$ is selected from the group consisting of hydrogen, alkyl, aryl, cycloalkyl, arylalkyl, and alkylaryl, with the proviso that when R is —OR$_3$, then R$_3$ is not hydrogen, or when R is —OC(O)N(R$_3$)$_2$, then R$_3$ is not aryl, or when R is —OC(O)R$_3$, then R$_3$ is not alkyl, and in which FG' is selected from the group consisting of —OR$_3$, —SR$_3$, —SiH$_2$R$_3$—OC(O)N(R$_3$)$_2$, —OC(O)C(=CHR$_3$)R$_3$, —OC(O)R$_3$, —C(O)R$_3$, —N(R$_3$)$_2$, —C(O)OR$_3$, —NCO, —C(O)N(R$_3$)$_2$, —OC(O)OR$_3$, —CN, halogen, sulfonic acid, and quaternary ammonium, or (c2) when R is oxygen, sulfur, nitrogen or —SiH$_2$—, FG is selected from the group consisting of hydrogen, alkyl, aryl, cycloalkyl, alkylaryl, arylalkyl, alkyl-FG", and aryl-FG", wherein FG" is the same as FG' as defined in (c1) above, or (c3) FG is a functional group as defined in (c1) in combination with a polyethylene glycol derived spacer group linking said maleimide unit with at least one other maleimide unit to form a di- or multifunctional maleimide compound.

9. The composition of claim 8, wherein said maleimide compound is selected from the group consisting of:

triethylene glycol biscarbonate bisethylmaleimide (TEGBCBEMI)

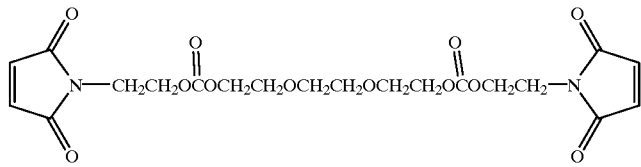

2-ethylcarbonate ethylmaleimide (2ECEMI)

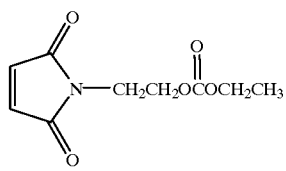

2-isopropyl urethane ethylmaleimide (2IPUEMI)

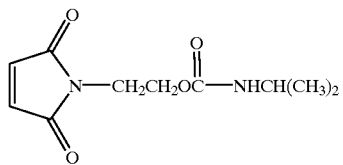

2-acryloyl ethylmaleimide (2AEMI)

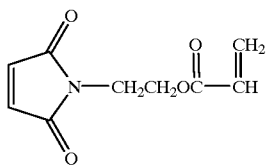

isophorone bisurethane bisethylmaleimide (IPBUBEMI)

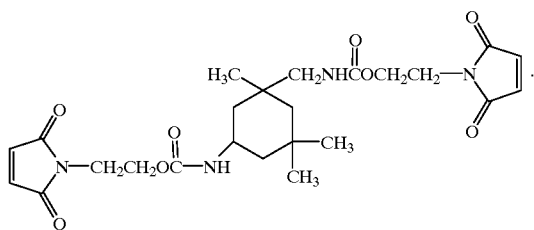

10. The composition of claim 8, wherein said photopolymerizable vinyl compound is selected from the group consisting of monomers and oligomers derived from acrylic and methacrylic acid, optionally dispersed or dissolved in a solvent copolymerizable therewith.

11. The composition of claim 8, wherein said photopolymerizable compound is selected from the group consisting of methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, hydroxy acrylates, glycol acrylates, allyl acrylates, epoxy acrylates, aminoplast acrylates, acrylated epoxides, acrylated polyesters, acrylated polyurethanes, and mixtures thereof.

12. The composition of claim 8, wherein said maleimide compound comprises a compound of the formula:

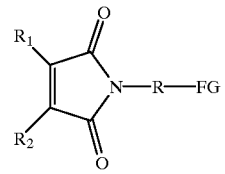

wherein R is linear or branched C1 to C10 alkylene and FG is a functional group selected from the group consisting of —$OR_3$, —$SR_3$, —$SiH_2R_3$, —$OC(O)N(R_3)_2$, —$OC(O)C(=CHR_3)R_3$, —$OC(O)R_3$, —$C(O)R_3$, —$N(R_3)_2$, —$C(O)OR_3$, —NCO, —$C(O)N(R_3)_2$, —$OC(O)OR_3$, —CN, halogen, —$CH_2$N-aryl-FG', —$CH_2$N-aryl-$R_3$-FG', sulfonic acid, quaternary ammonium, and salts thereof, in which each $R_3$ is selected from the group consisting of hydrogen, alkyl, aryl, cycloalkyl, arylalkyl, and alkylaryl, with the proviso that when R is —$OR_3$, then $R_3$ is not hydrogen, or when R is —$OC(O)N(R_3)_2$, then $R_3$ is not aryl, or when R is —$OC(O)R_3$, then $R_3$ is not alkyl, and in which FG' is selected from the group consisting of —$OR_3$, —$SR_3$, —$SiH_2R_3$, —$OC(O)N(R_3)_2$, —$OC(O)C(=CHR_3)R_3$, —$OC(O)R_3$, —$C(O)R_3$, —$N(R_3)_2$, —$C(O)OR_3$, —NCO, —$C(O)N(R_3)_2$, —$OC(O)OR_3$, —CN, halogen, sulfonic acid, and quaternary ammonium.

13. The composition of claim 8, wherein said maleimide compound comprises a compound of the formula:

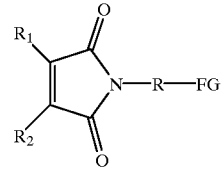

wherein R is oxygen, sulfur, nitrogen or —$SiH_2$— and FG is selected from the group consisting of hydrogen, alkyl, aryl, cycloalkyl, alkylaryl, arylalkyl, alkyl-FG", and aryl-".

14. The composition of claim 8, wherein said maleimide compound comprises a compound of the formula:

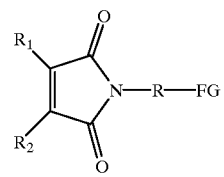

wherein R is linear or branched C1 to C10 alkylene, oxygen, sulfur, nitrogen, or —$SiH_2$— and FG is a functional group selected from the group consisting of —$OR_3$, —$SR_3$, —$SiH_2R_3$, —$OC(O)N(R_3)_2$, —$OC(O)C(=CHR_3)R_3$, —$OC(O)R_3$, —$C(O)R_3$, —$N(R_3)_2$, —$C(O)OR_3$, —NCO, —$C(O)N(R_3)_2$, —$OC(O)OR_3$, —CN, halogen, —$CH_2$N-aryl-FG', —$CH_2$N-aryl-$R_3$-FG', sulfonic acid, quaternary ammonium, and salts thereof in combination with a polyethylene glycol derived spacer group linking said maleimide unit with at least one other maleimide unit to form a di- or multifunctional maleimide compound.

* * * * *

UNITED STATES PATENT AND TRADEMARK OFFICE
CERTIFICATE OF CORRECTION

PATENT NO. : 6,034,150
DATED : March 7, 2000
INVENTOR(S) : Hoyle et al

It is certified that error appears in the above-indentified patent and that said Letters Patent is hereby corrected as shown below:

Column 12, line 46, after"exposing" insert --a--.

Column 16, line 17, "c10 alkylene" should read --C10 alkyl--;

Column 18, line 38, "aryl-" should read --aryl-FG"--.

Signed and Sealed this

Thirteenth Day of March, 2001

Attest:

NICHOLAS P. GODICI

Attesting Officer    Acting Director of the United States Patent and Trademark Office